United States Patent [19]
Claverie et al.

[11] 3,968,214
[45] July 6, 1976

[54] 5-METHYLTHIO-PYRIMIDINE VASODILATORS

[75] Inventors: Jean-Marie Claverie, Enghien-les-Bains; Gérard Loiseau, Sceaux; Georges Mattioda, Enghien-les-Bains; René Millischer, Pringy; Francois Percheron, Brevannes, all of France

[73] Assignee: Produits Chimiques Ugine Kuhlmann, Paris, France

[22] Filed: Oct. 12, 1973

[21] Appl. No.: 406,129

[30] Foreign Application Priority Data
July 6, 1973 France .............................. 73.24875

[52] U.S. Cl. ..................... 424/251; 260/247.1 M; 260/256.5 R; 424/248
[51] Int. Cl.² ..................................... A61K 31/505
[58] Field of Search ............. 260/256.5 R; 424/251, 424/248

[56] References Cited
UNITED STATES PATENTS
3,817,998   6/1974   Anderson et al. .............. 424/248 X

*Primary Examiner*—Leonard Schenkman
*Attorney, Agent, or Firm*—Beveridge, DeGrandi, Kline & Lunsford

[57] ABSTRACT

The compounds of the formula:

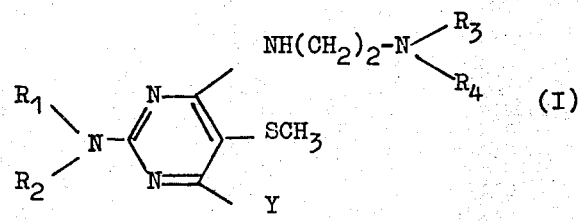

in which Y represents a chlorine atom or an alkoxy, dialkylaminoalkoxy, pyridylalkoxy group, $R_1$ and $R_2$ are identical or different substituents and represent alkyl or alkoxycarbonylalkyl groups, substituted or unsubstituted phenyl groups or form together with the nitrogen atom to which they are attached, a heterocyclic ring which may contain another hetero-atom, $R_3$ and $R_4$ are identical or different substituents and represent alkyl groups or form, together with the nitrogen atom to which they are attached, a heterocyclic ring which may contain another hetero-atom; process for their preparation; medicaments comprising such compounds or salts thereof, and their use in the treatment of human beings.

13 Claims, No Drawings

5-METHYLTHIO-PYRIMIDINE VASODILATORS

The present invention relates to new pyrimidines, to their use as medicaments on account of their spasmolytic, coronary dilator and hypoglycemiant properties and to their preparation.

These compounds, derived from 5-methylthio-pyrimidine, may be represented by the general formula:

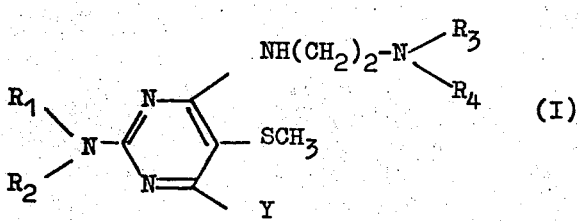

in which Y represents a chlorine atom or an alkoxy, dialkylaminoalkoxy or pyridylalkoxy group, the alkoxy and alkyl groups preferably containing 1 to 4 carbon atoms, $R_1$ and $R_2$ are identical or different substituents and represent alkyl, alkoxycarbonylalkyl, substituted or unsubstituted phenyl or benzyl groups or form, together with the nitrogen atom to which they are attached, a heterocyclic ring which may contain another hetero-atom, the alkyl and alkoxy groups preferably containing 1 to 4 carbon atoms, $R_3$ and $R_4$ are identical or different substituents and represent alkyl groups preferably containing 1 to 4 carbon atoms or form, together with the nitrogen atom to which they are attached, a heterocyclic ring which may possibly contain another hetero-atom.

Substituents of the phenyl group may be for example halogen atoms or alkyl, alkoxy or trihalomethyl groups.

The compounds of formula (I) may be prepared for example by reacting a compound of the formula:

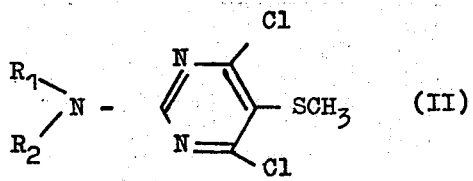

in which $R_1$ and $R_2$ have the same significance as above, with an ethylenediamine of the formula:

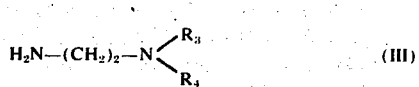

in which $R_3$ and $R_4$ have the same significance as above, and possibly replacing the remaining chlorine atom by an alkoxy, dialkylamino-alkoxy or pyridylalkoxy group.

The reaction with the compound of formula (III) is preferably effected in a solvent, in the presence of an acid-absorbing agent, at a temperature between 20°C. and 100°C.

The substitution of the remaining chlorine atom may be effected for example by the action of an alcoholate of an alkali metal or by the action of an excess of the corresponding alcohol and caustic potash at the refluxing temperature.

The invention is illustrated by the following Examples, in which the parts are parts by weight, unless the contrary is indicated. Preceding the Examples are Preparations 1 to 12 which are concerned with the preparation of the compounds of formula (II).

PREPARATION 1

60 parts by volume of benzene, 10 parts of 2,4,6-trichloro-5-methylthio-pyrimidine and 4.85 parts of triethylamine are placed in an apparatus. After heating under reflux for three hours, the reaction product is filtered, concentrated, and and recrystallised from alcohol. 7.9 parts of 2-N,N-diethylamino-4,6-dichloro-5-methylthio-pyrimidine of melting point 48°C. are obtained.

PREPARATIONS 2 TO 7

On operating as in Preparation 1, but using tripropylamine, N,N-(diethyl)-N-(ethoxycarbonylmethyl)amine, N-methyl-piperidine, N-methylmorpholine, N,N-dimethyl-N-benzylamine, and N-methyl-N,N-dibenzylamine instead of the triethylamine, the following compounds are respectively obtained:

| Preparations | | M.p. |
|---|---|---|
| 2 | 2-dipropylamine-5-methylthio-4,6-dichloro-pyrimidine | 71°C. |
| 3 | 2-N-ethyl-N-(ethoxycarbonylmethyl)amino-5-methylthio-4,6-dichloropyrimidine | 106°C. |
| 4 | 2-piperidino-5-methylthio-4,6-dichloro-pyrimidine | 71°C. |
| 5 | 2-morpholino-5-methylthio-4,6-dichloro-pyrimidine | 116°C. |
| 6 | 2-N,N-dimethylamino-5-methylthio-4,6-dichloro-pyrimidine | 74°C. |
| 7 | 2-N-methyl-N-benzylamino-5-methylthio-4,6-dichloro-pyrimidine | 73°C. |

PREPARATION 8

23 parts of 2,4,6-trichloro-5-methylthio-pyrimidine, 15 parts of N,N-dimethylaniline and 0.05 parts of potassium iodide are mixed and heated until a very dark colour is obtained. The product crystallises on cooling, 25 parts of water and 50 parts by volume of 3N hydrochloric acid are added, and the product is filtered off, dried and recrystallised from ethyl alcohol. 27 parts of 2-N-methylphenylamino-4,6-dichloro-5-methylthio-pyrimidine of melting point 99°C. are obtained.

The following Table gives examples of compounds obtained in a similar way from particular N,N-dimethylanilines.

| Preparations | | M.p. |
|---|---|---|
| 9 | 2-N-methyl-N(4-chloro-phenyl)amino-4,6-dichloro-5-methylthio-pyrimidine | 130°C. |
| 10 | 2-N-methyl-N(4-methyl-phenyl)amino-4,6-dichloro-5-methylthio-pyrimidine | 111°C. |
| 11 | 2-N-methyl-N(3-trifluoromethyl-phenyl)-amino-4,6-dichloro-5-methylthio-pyrimidine | 117°C. |
| 12 | 2-N-methyl-N(3,4-dimethoxy-phenyl)amino-4,6-dichloro-5-methylthio-pyrimidine | 151°C. |

EXAMPLE 1

23.8 parts of 2-dimethylamino-4,6-dichloro-5-methylthio-pyrimidine are placed in 300 parts by volume of benzene and a solution of 12.2 parts of N,N-diethylethylenediamine and 16 parts of triethylamine is added. The mixture is heated under reflux for three hours. After filtering off the triethylamine hydrochloride, the mixture is concentrated, extracted with ether/water, and the organic phase is concentrated and recrystalised from ethyl alcohol. 2-dimethylamino-4-(2'-diethylamine)ethylamino-5-methylthio-6-chloropyrimidine having a melting point of 56°C. is obtained.

The following products have been obtained in the same way either in the form of the base or in the form of the mono- or di-hydrobromide.

| Examples | | | M.p. |
|---|---|---|---|
| 2 | 2-N-methyl-N-phenylamino-4-(2'-diethylamino)-ethylamino-5-methylthio-6-chloro-pyrimidine | 2HBr | 162°C. |
| 3 | 2-diethylamino-4-(2'-diethylamino)-ethylamino-5-methylthio-6-chloro-pyrimidine | 2HBr | 110°C. |
| 4 | 2-N-methyl-N-benzylamino-4-(2'-diethylamino)-ethylamino-5-methylthio-6-chloro-pyrimidine | HBr | 136°C. |
| 5 | 2-dipropylamino-4-(2'-diethylamino)-ethylamino-5-methylthio-6-chloro-pyrimidine | 2HBr | 160°C. |
| 6 | 2-N-methyl-2-N-(4-chloro-phenyl)amino-4-(2'-diethylamino)-ethylamino-5-methylthio-6-chloro-pyrimidine | HBr | 197°C. |
| 7 | 2-N-methyl-N-phenyl-amino-4-(2'-dimethylamino)-ethylamino-5-methylthio-6-chloro-pyrimidine | HBr | 182°C. |
| 8 | 2-dimethylamino-4-(2'-dimethylamino)-ethylamino-5-methylthio-6-chloro-pyrimidine | | 69°C. |
| 9 | 2-morpholino-4-(2'-dimethylamino)-ethylamino-5-methylthio-6-chloro-pyrimidine | | 80°C. |
| 10 | 2-N-methyl-N-(ethoxycarbonylmethyl)-amino-4-(2'-dimethylamino)-ethylamino-5-methylthio-6-chloro-pyrimidine | | 64°C. |
| 11 | 2-N-methyl-N-benzylamino-4-(2'-di-isopropyl-amino)-ethylamino-5-methylthio-6-chloro-pyrimidine | | 70°C. |
| 12 | 2-N-methyl-N-phenylamino-4-(2'-di-isopropyl-amino)-ethylamino-5-methylthio-6-chloro-pyrimidine | HBr | 163°C. |
| 13 | 2-piperidino-4-(2'-diisopropylamino)-ethylamino-5-methylthio-6-chloro-pyrimidine | HBr | 202°C. |
| 14 | 2-N-methyl-N(4-methyl-phenyl)amino-4-(2'-diisopropylamino)-ethylamino-5-methylthio-6-chloro-pyrimidine | | 99°C. |
| 15 | 2-N-methyl-N-(ethoxycarbonylmethyl)-amino-4-(2'-diisopropylamino)-ethylamino-5-methyl-thio-6-chloro-pyrimidine | HBr | 172°C. |
| 16 | 2-diethylamino-4-(2'-diisopropylamino)-ethylamino-5-methylthio-6-chloro-pyrimidine | HBr | 188°C. |
| 17 | 2-N-methyl-N(3-trifluoromethyl-phenyl)-amino-4-(2' -diisopropylamino)-ethylamino-5-methylthio-6-chloro-pyrimidine | HBr | 190°C. |
| 18 | 2-N-methyl-N(4-chloro-phenyl)amino-4-(2'-diisopropyl-amino)-ethylamino-5-methylthio-6-chloro-pyrimidine | HBr | 192°C. |
| 19 | 2-N-methyl-N(4-methyl-phenyl)amino-4-(2'-diethylamino)-ethylamino-5-methyl-thio-6-chloro-pyrimidine | HBr | 150°C. |
| 20 | 2-N-methyl-N(3,4-dimethoxy-phenyl)amino-4-(2'-diethylamino)-ethylamino-5-methylthio-6-chloro-pyrimidine | HBr | 205°C. |
| 21 | 2-N-methyl-N(3,4-dimethoxy-phenyl)amino-4-(2'-diisopropylamino)-ethylamino-5-methylthio-6-chloro-pyrimidine | | 80°C. |
| 22 | 2-N-methyl-N-(4-chloro-phenyl)amino-4-(2'-2,6-dimethyl-morpholino)-ethylamino-5-methylthio-6-chloro-pyrimidine | | 104°C. |

EXAMPLE 23

25 parts of 3-pyridine-methanol and 6 parts of caustic potash are mixed and heated. After formation of the potassium salt, 19.5 parts of 2-N-dimethylamino-4-(2'-dimethyl-amino)-ethylamino-5-methylthio-6-chloropyrimidine are introduced. The mixture is heated at about 130°–140°C. for 3 hours, then taken up in water and in ether, and the organic phase is concentrated. The oily product formed is dissolved in alcohol, and 20 parts by volume of concentrated hydrobromic acid are added. The product precipitates and is recrystallised from alcohol. The hydrobromide of 2-N-dimethyl-amino-4-(2'-dimethylamino)-ethylamino-5-methyl-thio-6-(3-pyridyl)-methoxy-pyrimidine of melting point 180°C. is obtained with a yield of 58%.

The product is concentrated in vacuo, washed with ether/water, and the organic phase is concentrated. The residual oil is dissolved in acetone. 24 parts by volume of hydrobromic acid are added and the product is precipitated with ether. On purification, the dihydrobromide of 2-N-methyl-N,phenylamino-4-(2'-diisopropylamino)-ethylamino-5-methyl-thio-6-methoxy-pyrimidine of melting point 176°C. is obtained with a yield of 50 %.

The following products have been prepared according to the processes of the preceding Examples:

| Examples | | | M.p. |
|---|---|---|---|
| 25 | 2-N-methyl-N(4-chloro-phenyl)amino-4-(2'-diethylamino)-ethylamino-5-methylthio-6-methoxy-pyrimidine | HBr | 175°C. |
| 26 | 2-N-methyl-N-phenyl-amino-4-(2'-dimethylamino)-ethylamino-5-methylthio-6-methoxy-pyrimidine | HBr 0.5 H₂O | 167°C. |
| 27 | 2-N-methyl-N-benzyl-amino-4-(2'-diisopropyl-amino)-ethylamino-5-methyl-thio-6-methoxy-pyrimidine | | 64°C. |
| 28 | 2-N-methyl-N-(3,4-dimethoxy-phenyl)-amino-4-(2'-diisopropyl-amino)-ethyl-amino-5-methylthio-6-methoxy-pyrimidine | HBr | 198°C. |
| 29 | 2-piperidino-4-(2'-diisopropyl-amino)-ethylamino-5-methylthio-6-methoxy-pyrimidine | HBr | 184°C. |
| 30 | 2-N-methyl-N-phenyl-amino-4-(2'-di-isopropyl-amino)-ethylamino-5-methyl-thio-6-(dimethylaminoethyl)-methoxy-pyrimidine | 2HBr | 198°C. |
| 31 | 2-N-methyl-2-N-benzylamino-4-(2'-di-isopropyl-amino)-ethylamino-5-methylthio-6-butoxy-pyrimidine | HBr | 112°C. |
| 32 | 2-N-methyl-N-phenylamino-4-(2'-diisopropyl-amino)-ethylamino-5-methyl-thio-6-butoxy-pyrimidine | HBr | 169°C. |

EXAMPLE 24

40.7 parts of 2N-methyl-N-phenyl-amino-4-(2'-diisopropylamino)-ethylamino-5-methylthio-6-chloro-pyrimidine in 200 parts by volume of methanol and 7 parts of caustic potash are placed in an autoclave, and the mixture is heated at between 120°C. and 130°C. for 3 hours.

TOXICOLOGICAL PROPERTIES

The acute toxicities of the compounds according to the invention have been determined CD 1 mice (Charles RIVER) by intravenous and oral methods. The LD50 calculated by the quantal cumulative method of J. J. Reed and H. Muench (Amer. J. Hyg. 1938, 27, 493) are collected in the following Table:

| | | Acute toxicity to mice LD 50 (mg/kg) | |
|---|---|---|---|
| | | intravenous | orally |
| Product of Example | 1 (base) | 53 | 200 |
| " | 2 (2HBr) | 43 | 225 |
| " | 3 (2HBr) | 64 | 225 |
| " | 4 (base) | 45 | 525 |
| " | 5 (2HBr) | — | 800 |
| " | 6 (HBr) | — | 610 |
| " | 7 (HBr) | 80 | 200 |
| " | 8 (base) | 57 | 525 |
| " | 9 (base) | — | 400 |
| " | 10(base) | 79 | 900 |
| " | 11(base) | 60 | 675 |
| " | 12(HBr) | | 600 |
| " | 13(HBr) | — | over 900 |
| " | 14(base) | 92 | 900 |
| " | 15(HBr) | 63 | over 900 |
| " | 16(HBr) | — | 600 |
| " | 17(HBr) | — | atoxic 900 |
| " | 18(HBr) | — | over 900 |
| " | 19(HBr) | — | about 675 |
| " | 20(HBr) | — | 400 |
| " | 21(base) | — | about 600 |
| " | 22(base) | — | atoxic 900 |
| " | 23(2HBr) | 22 | 175 |
| " | 24(2HBr) | 22 | 600 |
| " | 25(HBr) | — | about 600 |
| " | 26(HBr) | 70 | 225 |
| " | 27(base) | 18.5 | 600 |
| " | 28(HBr) | — | about 200 |
| " | 29(HBr) | — | " 200 |
| " | 30(2HBr) | 9.5 | 200 |
| " | 31(HBr) | — | about 675 |
| " | 32(HBr) | — | about 525 |

On the whole, the products according to the invention are not very toxic to mice since, taken orally, many are atoxic at 900 mg/kg and others have an LD 50 between 175 and more than 900 mg/kg.

PHARMACOLOGICAL PROPERTIES

1. Analgesic and antiserotonin activity:

The analgesic activities have been investigated with respect to abdominal spasms caused in mice by the intraperitoneal injection of 2-phenyl-1,4-benzoquinone according to E. Siegmund, E. Cadmus and G. Lu, Proc. Soc. exp. Biol. Med., 1957, 95, 729–731. The central antiserotonin properties have been determined by the "Head-twitch" technique in mice according to S. J. Corne, R. W. Pickering and B. T. Warner, Brit. J. Pharmacol., 1963, 20, 106–120. In this test, the antiserotonin products inhibit the sudden shaking of the head induced in mice by 5-hydroxy-tryptophan, the biological precursor of serotonin.

| Product of Example | Mice Analgesic activity P.B.Q. AD 50 (mg/kg) oral | Antiserotonin activity Head-twitch AD 50 (mg/kg) oral |
|---|---|---|
| 2 | over 100 | 95 |
| 3 | over 100 | 35 |
| 5 | over 300 | 100 |
| 6 | — | 65 |
| 7 | 60 | — |
| 12 | 100 | — |
| 13 | — | 185 |
| 16 | 70 | 90 |
| 17 | — | 400 |
| 18 | over 300 | 205 |
| 26 | 65 | — |
| 27 | 95 | — |

When given orally to mice, the compounds of Examples 7, 16 and 27 exert a marked analgesic activity, while those of Examples 2, 3, 6 and 16 are central antiserotonine.

2. Spasmolytic activities

The spasmolytic activities are known by means of the technique of R. Magnus (Arch. Ges. Physiol., 1904, 102, 123) on the isolated duodenum of rabbits. The spasmolytic neurotropes inhibit the contractions of the organ caused by acetylcholine, while the musculotropes prevent the spasms induced by barium chloride. The EC 50 expressed in mg/litre are collected in the following Table where EC denotes "Effective concentration".

| Products of Examples | Spasmolytic activities EC 50 (mg/l) isolated duodenum of rabbit | |
|---|---|---|
| | Neurotrope versus acetylcholine | Musculotrope versus BaCl$_2$ |
| 1 | 5.50 | 1.40 |
| 2 | 1.50 | 0.80 |
| 3 | 1.30 | 0.30 |
| 4 | 0.30 | 0.06 |
| 5 | 1.00 | 0.90 |
| 7 | 1.20 | 0.16 |
| 8 | 4.90 | 2.80 |
| 9 | 3.00 | 1.90 |
| 10 | 0.50 | 0.50 |
| 11 | 3.50 | 0.02 |
| 14 | 0.08 | 0.04 |
| 15 | — | 0.05 |
| 16 | — | 0.30 |

-continued

| Products of Examples | Spasmolytic activities EC 50 (mg/l) isolated duodenum of rabbit | |
|---|---|---|
| | Neurotrope versus acetylcholine | Musculotrope versus BaCl$_2$ |
| 17 | — | 0.50 |
| 23 | 8.60 | 1.00 |
| 24 | 0.12 | 0.13 |
| 27 | — | 0.08 |
| 30 | — | 1.00 |

The products according to the invention show interesting neurotropic and musculotropic spasmolytic properties. From the point of view of neurotropic activity, it is necessary to call attention to the products of Examples 4, 10, 14 and 24 while from the point of view of musculotropic effects, the products of Examples 4, 11, 14, 15 and 27 exert quite remarkable activities with EC 50 less than 0.1 mg/liter.

3. Coronaro-dilatatory activities

The technique of Langendorff, modified by F. E. Anderson, (J. Pharmacol. exp. Therap., 1948, 91, 135) using isolated rabbit heart permits the coronaro-dilatatory activity of the products to be studied. In this text, the cardiac perfusion liquid contains 0.5 UI/1 of post-hypophysis. The results are expressed in the percentage variation of the coronary flow after affusion of the product to be tested, compared with the initial flow.

| Products of Examples | Coronaro-dilatatory effect | |
|---|---|---|
| | Dose in mg | Increase of the coronary flow in % |
| 2 | 0.01 | +56 |
| | 0.03 | +58 |
| | 0.10 | +64 |
| | 0.30 | +91 |
| 4 | 0.003 | +8 |
| | 0.010 | +28 |
| | 0.030 | +41 |
| | 0.100 | +135 |
| 7 | 0.003 | +38 |
| | 0.010 | +40 |
| | 0.030 | +37 |
| | 0.100 | +77 |
| 11 | 0.001 | +168 |
| | 0.003 | +172 |
| 14 | 0.003 | +104 |
| | 0.010 | +140 |
| | 0.030 | +168 |
| 15 | 0.003 | +16 |
| | 0.010 | +24 |
| | 0.030 | +44 |
| | 0.100 | +28 |
| 16 | 0.003 | +16 |
| | 0.010 | +52 |
| 24 | 0.003 | +26 |
| | 0.01 | +32 |
| | 0.03 | +58 |
| | 0.10 | +67 |

In this test, the products of Examples 2, 4, 7, 15, 16 and 24 and especially those of Examples 11 and 14 exert interesting coronaro-dilatatory activities.

4. Hypoglycemiant properties

The hypoglycemiant properties have been studied on the male CD rats (Charles RIVER) weighing 200 to 250 g, in which the glycemia is controlled before treatment and then after 4 days of daily oral treatment. The seric glucose is determined by the method of W. S. Hoffmann (J. Biol. Chem., 1937, 120, 51). Groups of 10 rats are used and the hypoglycemiant activity is expressed by the percentage variation of the average glycemia of the treated animals with respect to that of the controls. If it is necessary, the statistical significance of the difference is determined by the test of the coefficient "$t$" of Student. The results are collected in the following Table.

| Product of Example | Hypoglycemiant activity in the rat | |
|---|---|---|
| | Dose mg/kg taken orally | Variation of the glycemia in % with respect to the controls |
| 5 | 300 | − 23+++ |
| 6 | 300 | − 36+++ |
| 7 | 100 | − 10+ |
| 11 | 300 | − 17+++ |
| 12 | 100 | − 24+++ |
| | 300 | − 38+++ |
| 13 | 300 | − 17+++ |
| 14 | 100 | − 8++ |
| 17 | 400 | − 22+++ |
| 18 | 300 | − 31+++ |
| 24 | 300 | − 34+++ |
| 30 | 100 | − 26+++ | significance of the variations:
+difference significant for p = 0.05
++difference significant for p = 0.01
+++difference significant for P = 0.001

Among these various products, those of Examples 5, 6, 12, 13, 17, 18, 24 and 30 have strong hypoglycemiant properties.

THERAPEUTIC APPLICATION

The products according to the invention may be used in human therapeutics as analgesics, anti-serotonins, spasmolytic musculotropes and neurotropes, vasodilators and especially coronary dilators, hypoglycemiants and anti-diabetics.

They may be administered for example in the form of compressed tablets, lozenges, gelatine-coated pills, cachets, suppositories, injectable ampoules or drops in unitary doses which comprise, according to the form and the compound used, between 10 mg and 500 mg, and according to a daily dose between 50 mg and 2500 mg.

We claim:

1. A pharmaceutical composition in unit dosage form suitable for use as a vasodilator comprising a pharmaceutically acceptable carrier and 10 mg to 500 mg of a compound of the formula:

$$R_1 \diagdown N \diagup N \diagdown NH-(CH_2)_2-N \diagup R_3 \diagdown R_4$$
$$R_2 \diagup \diagdown N= \diagdown Y \diagup SCH_3$$
(I)

in which Y represents chlorine, $R_1$ is methyl, $R_2$ is benzyl, phenyl, chlorophenyl, methyl phenyl, trifluoromethyl phenyl or 3,4-dimethoxy phenyl, $R_3$ and $R_4$ are the same and are selected from the group consisting of methyl, ethyl and isopropyl, or a salt thereof with a pharmaceutically acceptable acid.

2. A pharmaceutical composition according to claim 1 in which said compound is 2-N-methyl-N-phenylamino-4-(2′diethylamino)-ethylamino-5-methylthio-6-chloro-pyrimidine.

3. A pharmaceutical composition according to claim 1 in which said compound is 2-N-methyl-N-benzylamino-4-(2′diethylamino)-ethylamino-5-methylthio-6-chloro-pyrimidine.

4. A pharmaceutical composition according to claim 1 in which said compound is 2-N-methyl-2-N-(4-chloro-phenyl)amino-4-(2′-diethylamino)-ethylamino-5-methylthio-6-chloro-pyrimidine.

5. A pharmaceutical composition according to claim 1 in which said compound is 2-N-methyl-N-phenyl-amino-4-(2′-dimethyl-amino)-ethylamino-5-methylthio-6-chloro-pyrimidine.

6. A pharmaceutical composition according to claim 1 in which said compound is 2-N-methyl-N-benzylamino-4-(2′-diisopropyl-amino)-ethylamino-5-methylthio-6-chloro-pyrimidine.

7. A pharmaceutical composition according to claim 1 in which said compound is 2-N-methyl-N-phenylamino-4-(2′-di-isopropylamino)-ethylamino-5-methylthio-6-chloro-pyrimidine.

8. A pharmaceutical composition according to claim 1 in which said compound is 2-N-methyl-N(4-methyl-phenyl)amino-4-(2′-diisopropylamino)-ethylamino-5-methylthio-6-chloro-pyrimidine.

9. A pharmaceutical composition according to claim 1 in which said compound is 2-N-methyl-N(3-trifluoromethyl-phenyl)-amino-4-(2′-diisopropylamino)-ethylamino-5-methylthio-6-chloro-pyrimidine.

10. A pharmaceutical composition according to claim 1 in which said compound is 2-N-methyl-N(4-chloro-phenyl)amino-4-(2°-diisopropyl-amino)-ethylamino-5-methylthio-6-chloro-pyrimidine.

11. A pharmaceutical composition according to claim 1 in which said compound is 2-N-methyl-N(4-methyl-phenyl)amino-4-(2′-diethylamino)-ethylamino-5-methyl-thio-6-chloro-pyrimidine.

12. A pharmaceutical composition according to claim 1 in which said compound is 2-N-methyl-N(3,4-dimethoxy-phenyl)amino-4-(2′-diethylamino)-ethylamino-5-methylthio-6-chloro-pyrimidine.

13. A pharmaceutical composition according to claim 1 in which said compound is 2-N-methyl-N(3,4-dimethoxy-phenyl)amino-4-(2′-diisopropylamino)-ethylamino-5-methylthio-6-chloro-pyrimidine.

* * * * *